United States Patent
Ghosh et al.

(10) Patent No.: US 11,529,101 B2
(45) Date of Patent: Dec. 20, 2022

(54) METHOD TO QUANTIFY PHOTOPLETHYSMOGRAM (PPG) SIGNAL QUALITY

(71) Applicant: KONINKLIJKE PHILIPS N.V., Eindhoven (NL)

(72) Inventors: Erina Ghosh, Boston, MA (US); Cristhian Mauricio Potes Blandon, Salem, NH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1246 days.

(21) Appl. No.: 15/777,247

(22) PCT Filed: Nov. 10, 2016

(86) PCT No.: PCT/IB2016/056762
§ 371 (c)(1),
(2) Date: May 18, 2018

(87) PCT Pub. No.: WO2017/089921
PCT Pub. Date: Jun. 1, 2017

(65) Prior Publication Data
US 2018/0325457 A1 Nov. 15, 2018

Related U.S. Application Data

(60) Provisional application No. 62/259,308, filed on Nov. 24, 2015.

(51) Int. Cl.
*A61B 5/1455* (2006.01)
*A61B 5/00* (2006.01)
(Continued)

(52) U.S. Cl.
CPC .......... *A61B 5/7207* (2013.01); *A61B 5/0245* (2013.01); *A61B 5/02116* (2013.01);
(Continued)

(58) Field of Classification Search
CPC ....... A61B 5/1455; A61B 5/35; A61B 5/7207; A61B 5/02116; A61B 5/14552; A61B 5/7264; A61B 5/7246
See application file for complete search history.

(56) References Cited

U.S. PATENT DOCUMENTS

| 4,802,486 A | 2/1989 | Goodman |
| 5,241,964 A | 9/1993 | McQuilkin |

(Continued)

FOREIGN PATENT DOCUMENTS

| CN | 103020472 A | 4/2013 |
| CN | 104665768 A | 6/2015 |

(Continued)

OTHER PUBLICATIONS

Li, et al., "Dynamic time warping and machine learning for signal quality assessment of pulsatile signals"; Phys. Med, Sep. 2015.

*Primary Examiner* — Marjan Fardanesh

(57) ABSTRACT

When evaluating the quality of photoplethysmography (PPG) signal (52) measured from a patient monitor (e.g., a finger sensor or the like), multiple features of the PPG signal are extracted and analyzed to facilitate assigning a score to the PPG signal or portions (e.g., heartbeats) thereof. Heartbeats in the PPG signal are segmented out using concurrently captured electrocardiograph (ECG) signal (50), and for each heartbeat, a plurality of extracted features are analyzed. If all extracted features satisfy one or more predetermined criteria for each feature, then the heartbeat waveform is compared to a predefined heartbeat template. If the waveform matches the template (e.g., within a predetermined match percentage or the like), then the heartbeat is classified as "clean." If the heartbeat does not patch the template, or if one or more of the extracted features fails to satisfy its one or more pre-determined criteria, the heartbeat is classified as "noisy."

16 Claims, 4 Drawing Sheets

(51) Int. Cl.
    *A61B 5/021*     (2006.01)
    *A61B 5/0245*     (2006.01)
    *A61B 5/024*     (2006.01)
    *G06K 9/00*     (2022.01)
    *A61B 5/35*     (2021.01)
    *A61B 5/352*     (2021.01)

(52) U.S. Cl.
    CPC ...... *A61B 5/02125* (2013.01); *A61B 5/02416* (2013.01); *A61B 5/14552* (2013.01); *A61B 5/35* (2021.01); *A61B 5/352* (2021.01); *A61B 5/7203* (2013.01); *A61B 5/7221* (2013.01); *A61B 5/7246* (2013.01); *A61B 5/7264* (2013.01); *G06K 9/0053* (2013.01); *G06K 9/00543* (2013.01)

(56) References Cited

U.S. PATENT DOCUMENTS

| | | |
|---|---|---|
| 6,684,090 B2 | 1/2004 | Ali |
| 6,725,074 B1 | 4/2004 | Kastle |
| 2006/0224073 A1 | 10/2006 | Lin et al. |
| 2010/0081946 A1 | 4/2010 | Garudadri |
| 2010/0274102 A1 | 10/2010 | Teixeira |
| 2010/0324384 A1 | 12/2010 | Moon |
| 2012/0179011 A1 | 7/2012 | Moon |

FOREIGN PATENT DOCUMENTS

| | | |
|---|---|---|
| EP | 1977689 | 10/2008 |
| JP | H09215664 A | 8/1997 |
| JP | 2011180067 A | 9/2011 |
| KR | 101483756 B1 | 1/2015 |
| WO | 8605674 A1 | 10/1986 |
| WO | 2008065432 A1 | 6/2008 |
| WO | 2012108262 A1 | 8/2012 |
| WO | 2013036718 | 3/2013 |

METHOD TO QUANTIFY PHOTOPLETHYSMOGRAM (PPG) SIGNAL QUALITY

CROSS REFERENCE TO RELATED APPLICATIONS

This application is the U.S. National Phase application under 35 U.S.C. § 371 of International Application No. PCT/IB2016/056762, filed Nov. 10, 2016, published as WO 2017/089921 on Jun. 1, 2017, which claims the benefit of U.S. Provisional Patent Application No. 62/259,308 filed Nov. 24, 2015. These applications are hereby incorporated by reference herein.

The present invention finds application in patient monitoring systems and methods. However, it will be appreciated that the described techniques may also find application in other vital sign analysis systems, other patient measurement systems, and the like.

Photoplethysmography (PPG) is a method used to non-invasively measure blood volume changes during the cardiac cycle. PPG uses the change in absorption of light by tissues to measure the difference in oxygenation levels and infer the changes in blood volume. PPG is clinically used to measure the percentage of oxygenated saturation of blood (SpO2). PPG waveform analysis has also been used to calculate other clinical parameters such as pulse arrival time, estimate blood pressure etc. PPG measuring devices are small, portable and easy to use; hence they are widely used in hospitals and clinics to monitor patients.

A major challenge to PPG signal measurement and waveform interpretation is the inherent noise in the signal. The PPG signal is transiently affected by motion artifacts; therefore, the use of the signal as an input to various algorithms can lead to erroneous results. Although signal processing techniques and compensation strategies have been developed to overcome the noise issues of the PPG waveforms, there is no method to evaluate signal quality. Another challenge in evaluating PPG signal quality is the fact that most PPG devices output a filtered signal in which the signal amplitude has been modified (e.g., to scale for visualization purposes). Hence, PPG waveform magnitudes are difficult to interpret and this limits the evaluation of waveforms based on magnitude thresholds.

The present application provides new and improved systems and methods that facilitate automatically identifying and selecting clean segments of the PPG signal before PPG-derived parameters (e.g., pulse transit time, heart rate) are calculated and used in clinical decision support algorithms, thereby overcoming the above-referenced problems and others.

In accordance with one aspect, a system that facilitates automatically detecting segments of clean photoplethysmography (PPG) signal and rejecting noisy PPG signal segments comprises a patient monitor that concurrently records unfiltered PPG signal and electrocardiograph signal (ECG) of a patient, and a beat identification module configured to receive as input the unfiltered PPG signal and concurrent ECG signal from the patient monitor, and to segment each of a plurality of heartbeats in the PPG signal using the concurrently measured ECG signal. The system further comprises a PPG feature extraction module configured to extract a set of features for each heartbeat in the PPG signal, the features comprising one or more waveform amplitudes and one or more pulse transitions times (PPT), and a signal quality evaluation module configured to evaluate the extracted features and classify each PPG heartbeat waveform as clean or noisy. Additionally, the system comprises a processor configured to output, on a display, PPG signal statistics comprising identified clean PPG heartbeat waveforms for presentation to a user.

According to another aspect, a method for automatically detecting segments of clean photoplethysmography (PPG) signal and rejecting noisy PPG signal segments comprises receiving as input unfiltered PPG signal and concurrent ECG signal from a patient monitor, segmenting each of a plurality of heartbeats in the PPG signal using the concurrently measured ECG signal, and extracting a set of features for each heartbeat in the PPG signal, the features comprising one or more waveform amplitudes and one or more pulse transitions times (PPT). The method further comprises evaluating the extracted features and classifying each PPG heartbeat waveform as clean or noisy, and outputting, on a display, PPG signal statistics comprising identified clean PPG heartbeat waveforms for presentation to a user.

Still further advantages of the subject innovation will be appreciated by those of ordinary skill in the art upon reading and understand the following detailed description.

The drawings are only for purposes of illustrating various aspects and are not to be construed as limiting.

The ability to characterize the signal quality of PPG waveform over a period of time and to evaluate the quality of signal over smaller segments will be extremely useful when PPG signal is used to compute other clinical parameters. According to one embodiment, a framework is provided for evaluating PPG waveforms on a beat by beat basis. First, a set of features is derived from the PPG waveform for evaluation on a beat by beat basis. Since the actual amplitude of the PPG signal is unknown, amplitude-based features need not be used. Instead, temporal and/or shape based features are derived from the PPG waveform. Second, the set of features is used to provide an indicator of the quality of each beat and overall waveform. Additionally, different weights can be assigned to each feature, which allows for PPG signal quality metric tailored to different applications.

The PPG signal gives a measure of the oxygenation level of blood as a function of time. This information is an extremely useful vital sign which indicates patient condition. Additionally, the PPG signal can be used to estimate other vital signs such as blood pressure. The measurement of PPG signal can be performed in an unobtrusive and inexpensive manner, and therefore PPG is a very frequently measured vital sign. The subject innovation allows for automatic classification of the PPG signal into "clean" (i.e., usable) and "noisy" (unusable) beats to reliably measure blood oxygenation level and prediction of other parameters. The subject systems and methods can be employed in all clinical settings from the intensive care unit (ICU) to the emergency department (ED) and the doctor's office. The innovation automatically detects clean beats and uses these beats for further computations. Additionally, the innovation can be applied to algorithms and clinical decision support applications in which the PPG signal is used as an input.

Figure 1:
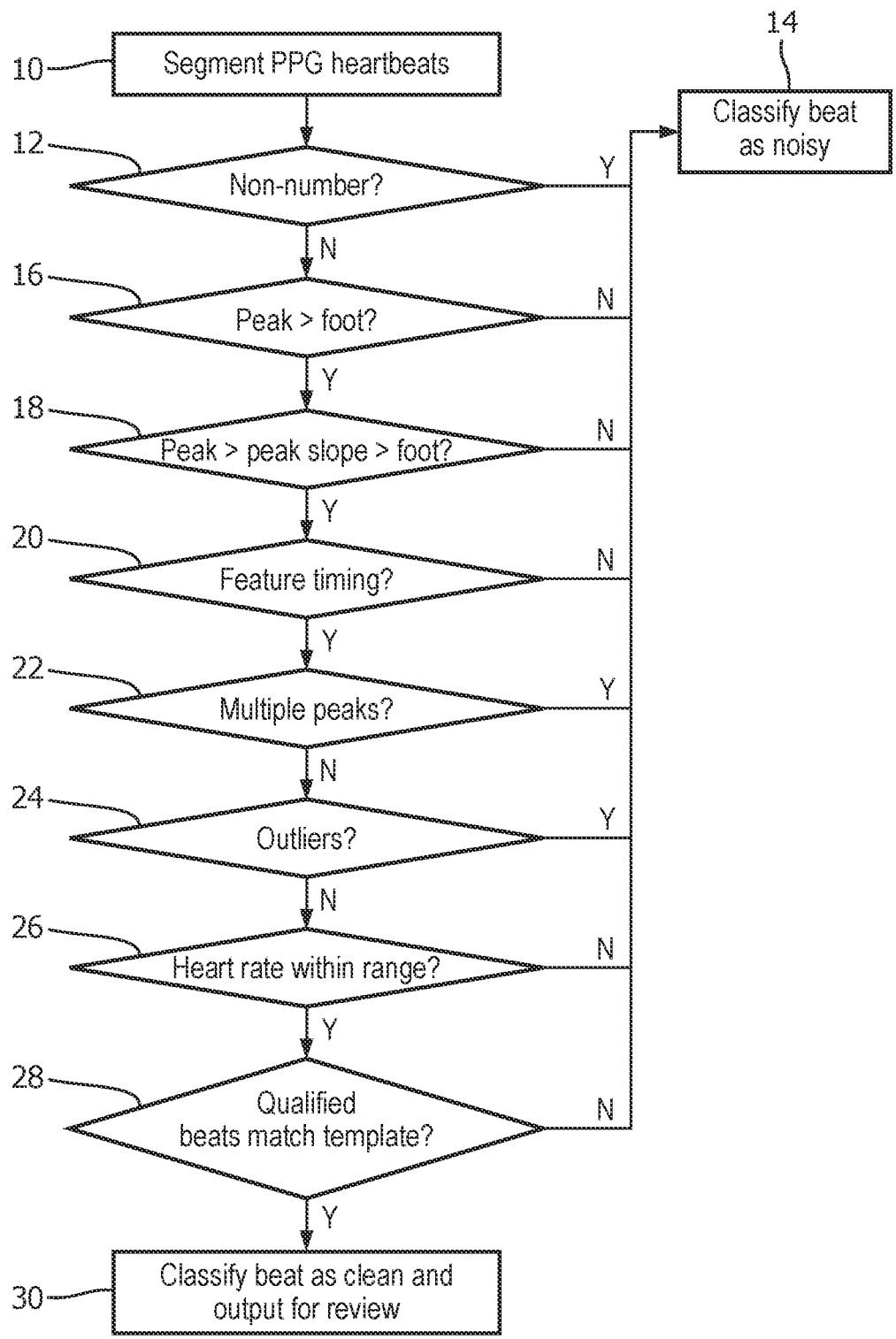
FIG. 1 illustrates a flow diagram that shows a method for automatically detect segments of clean PPG signal and reject noisy PPG signal segments.

FIG. 1 illustrates a flow diagram that shows a method for automatically detect segments of clean PPG signal and reject noisy PPG signal segments. Since the PPG signal is oscillatory, the time period of the signal is determined by the heart rate. Hence, electrocardiograph (ECG) derived R-peaks are used to segment the PPG signal into beats for further analysis. Accordingly, at 10 each of a plurality of heartbeats in a PPG waveform is segmented using an ECG signal. When performing heartbeat segmentation at 10, the ECG and PPG waveforms are simultaneously recorded. The time instance of each R peak from the ECG signal is estimated, and identified R peak indexes are used as the start point and end point of each beat. The PPG signal segment within each pair of consecutive R peaks is considered one PPG beat. A set of features derived from the PPG signal is identified, which can be used to classify whether a particular beat is "clean" or "noisy". Amplitude-based features need not be considered for beat classification since the amplitudes of the PPG signals recorded at the patient monitor are previously processed (e.g., amplitude values are scaled for visualization purposes). Rather, relative magnitude based features (e.g., amplitude of the peak relative to amplitude of the foot), time based features (see, e.g., FIG. 2) (e.g., time of the peak, time of the foot, and time of the peak slope), and/or shaped based features (e.g., beat matching) are used for beat classification.

At 12, a determination is made regarding whether the signal amplitude is a non-number value. If the signal amplitude is a non-number value (e.g., due to noisy or missing data), then at 14, the signal is classified as noisy. If the determination at 12 indicates that the signal amplitude is not noise (i.e., comprises a number value), then at 16 the relative magnitude of the peak amplitude is analyzed to determine whether the peak amplitude of the beat is greater than then amplitude at the foot of the beat. If this is not the case then the beat is classified as noisy at 14. If the peak amplitude is greater than the foot amplitude as determined at 16, then at 18 a determination is made regarding whether the peak amplitude of the beat is also greater than the amplitude at peak slope of the beat and whether the amplitude at the foot of the beat is smaller than the amplitude at peak slope of the beat. If these conditions are not satisfied then the beat is classified as noisy, at 14.

If the conditions are met at 18, at 20 a determination is made regarding whether wave feature timing meets predefined criteria. In a typical PPG beat (see, e.g., FIG. 2), the foot of the signal occurs before the peak slope, which occurs before the peak occurs. If this timing sequence is not seen in a particular beat, then the beat is classified as noisy at 14. If the timing of the wave feature meets the predefined criteria, then at 22 a determination is made regarding whether more than one peak is determined in the beat. If more than one peak is detected in a single beat then the beat is classified as noisy at 14.

If the determination at 22 indicates that only one peak is present in the beat, then at 24 outlier data in the time-based feature data is removed. For instance, a probability distribution (e.g., a histogram) is estimated for each of the features derived from the ECG and PPG signals (e.g., PTTp, PTTs, PTTf, etc.). In one embodiment, the 5th and 95th percentile for each of these distributions is calculated to define upper and lower thresholds. An outlier is identified if the value of a feature is below or above the corresponding threshold. Beats with outliers are classified as noisy, at 14.

For remaining beats, at 26, a determination is made regarding whether heart rate values are within a predetermined heart rate range. In one embodiment, the heart rate range ranges from 20 beats per minute to 200 beats per minute. However, it will be understood that any suitable range may be employed in conjunction with the various systems and methods described herein. Since PPG signal classification and quantification depends on ECG derived heart rate identification, heart rates beyond physiologic limits (i.e., the predetermined heart rate range) are rejected. Any beat with heart rate values outside this range is classified as noisy, at 14.

If the heart rate value is within the predetermined heart rate range, then at 28, beat matching is performed. The classification of beats in the PPG signal thus comprises two (or more) iterations. The first iteration (steps 10-26, explained above) is used to search for clean beat candidates across the PPG waveform. The second iteration 28 is used to refine the results as a final classification of beats. Thus, at 28, a "beat template" is calculated by first interpolating and low-pass filtering each beat candidate, and then by averaging all beat candidates together. This "beat template" is subsequently used for searching beats across the PPG waveform to identify beats that match the "beat template". Beats that pass the matching threshold are classified as "clean" beats, at 30.

Figure 2:
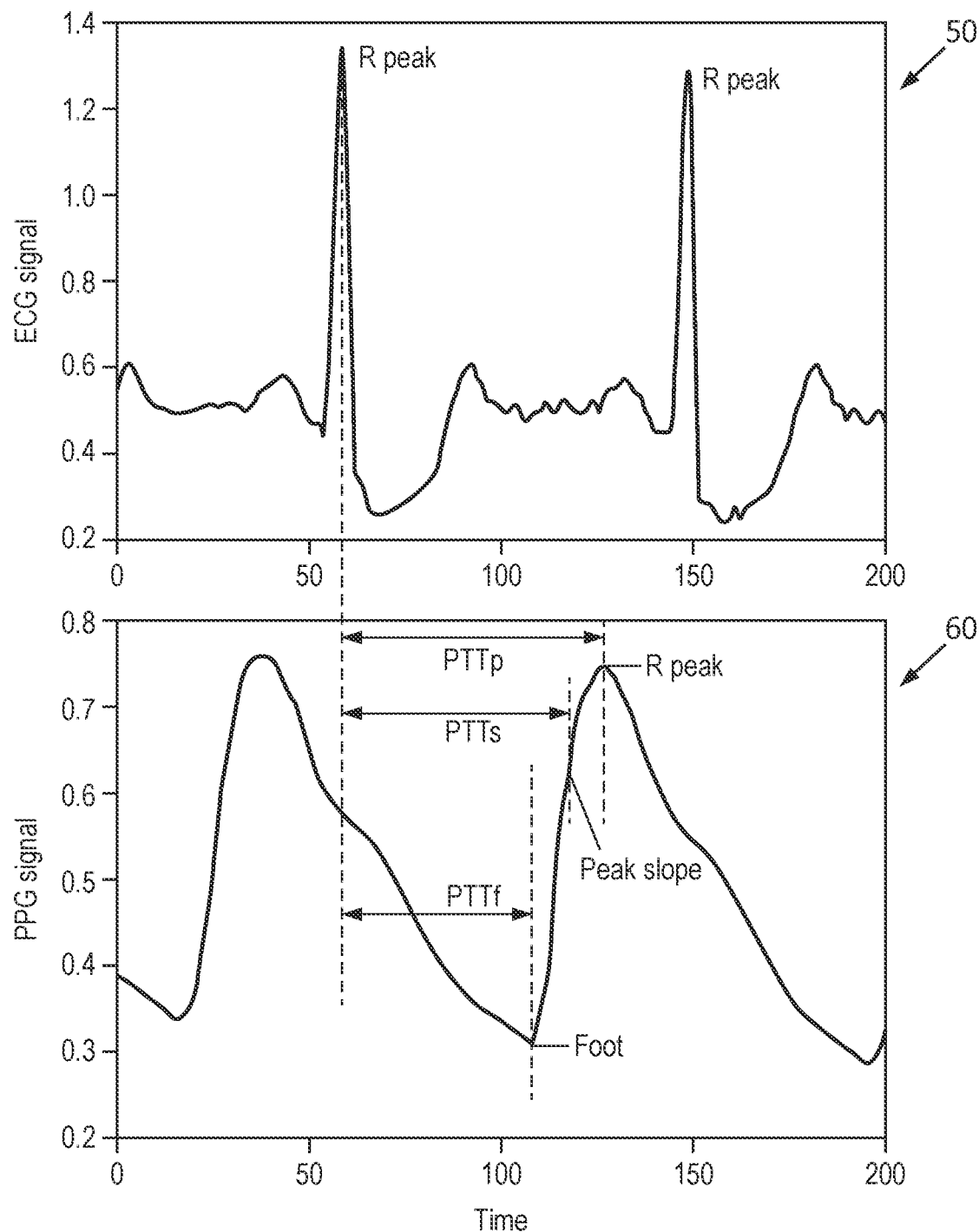
FIG. 2 illustrates an example of PPG feature calculation from ECG signal and PPG signal, in accordance with one or more features described herein.

FIG. 2 illustrates an example of PPG feature calculation from ECG signal 50 and PPG signal 52, in accordance with one or more features described herein. A peak pulse transit time (PTTp) is shown spanning the time between an R peak in the ECG signal 50 and the peak of an immediately subsequent PPG wave in the PPG signal 52. A slope pulse transit time (PTTs) is shown spanning the time between the R peak in the ECG signal 50 and a maximum slope of between the foot and peak of the immediately subsequent PPG wave in the PPG signal 52. A foot pulse transit time (PTTf) is shown spanning the time between the R peak in the ECG signal 50 and the foot of the immediately subsequent PPG wave in the PPG signal 52.

Figure 3:
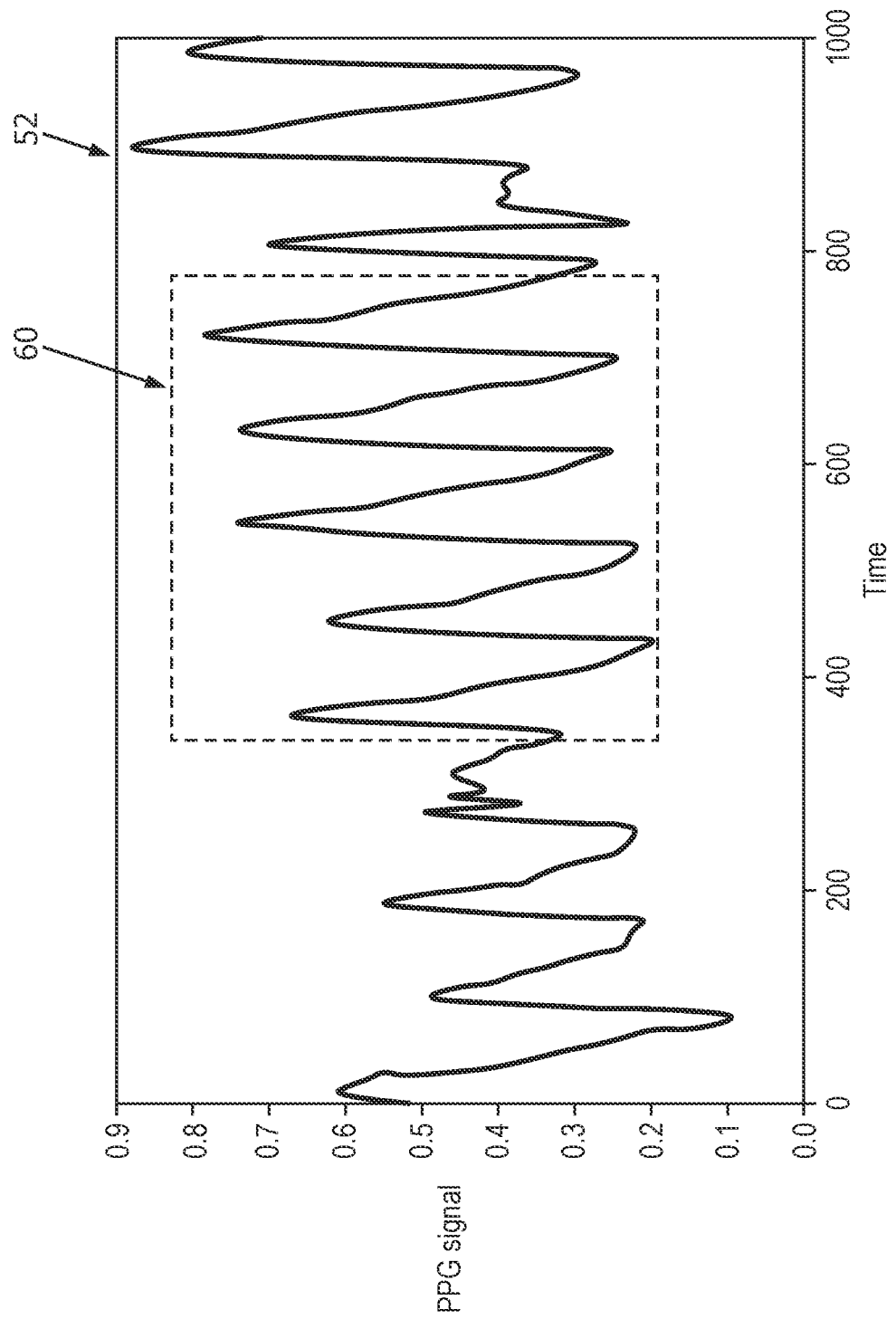
FIG. 3 illustrates a segment of the PPG signal classified as "clean" by the herein-described systems and methods.

FIG. 3 illustrates a segment 60 of the PPG signal 52 classified as "clean" by the herein-described systems and methods. The outcomes of the feature evaluations mentioned above are collected and the waveform quality is computed on a beat level. In one embodiment, each feature mentioned above classifies every beat as a clean or noisy beat. The overall quality of the beat is denoted as clean only if each of the evaluated features classifies the beat as clean. If the beat was classified as noisy by any single feature, then overall the beat is classified as noisy. Based on quality evaluation of each beat, the overall signal quality for the full waveform can be computed using the percentage of clean beats. In another embodiment, different weights can be attached to different features, which can be combined in ways that better reflect feature importance. This feature allows the framework to be customized for the application in which the PPG signal is used. The overall beat quality estimate can be, e.g., a range which can be used to better characterize the signal quality.

Figure 4:
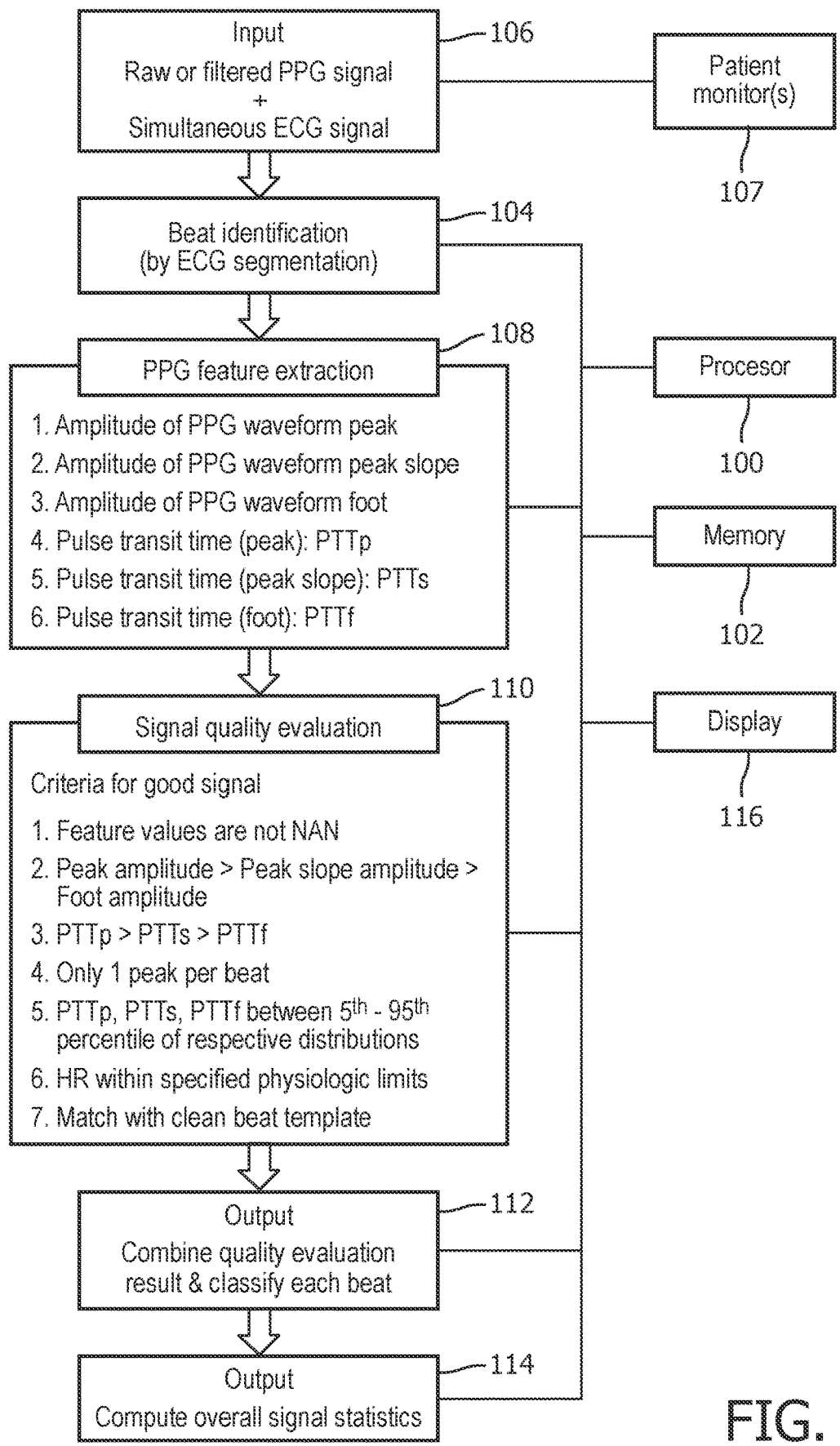
FIG. 4 illustrates a system that facilitates automatically detecting segments of clean PPG signal and rejecting noisy PPG signal segments.

FIG. 4 illustrates a system that facilitates automatically detecting segments of clean PPG signal and rejecting noisy PPG signal segments. The system comprises a processor 100 and a computer-readable medium or memory 102 configured to perform the various acts, methods, etc., described herein. The processor executes a beat identification module 104 that receives as input 106 raw or unfiltered PPG signal and concurrent or simultaneous ECG signal from one or more patient monitors 107 (e.g., an ECG monitor and an SpO2 monitor or the like). The beat identification module segments each of a plurality of heartbeats in a PPG waveform using the concurrently measured ECG signal. For purposes of heartbeat segmentation, the ECG and PPG waveforms are simultaneously recorded by the patient monitor 107. The time instance of each R peak from the ECG signal is estimated by the beat identification module, and identified R peak indexes are used as the start point and end point of each beat. The PPG signal segment within each pair of consecutive R peaks is considered one PPG beat.

Segmented beats are received by a PPG feature extraction module 108, which identifies a set of features derived from the PPG signal, which in turn can be used to classify whether a particular beat is "clean" or "noisy". The PPG feature extraction module extracts PPG signal features including but not limited to: amplitudes of the PPG waveform's peak, foot, and slope; and pulse transit times for the PPG waveform peak, foot, and slope (PTTp, PTTf, and PTTs, respectively). Amplitude-based features need not be considered for beat classification since the amplitudes of the PPG signals recorded at the patient monitor are previously processed (e.g., amplitude values are scaled for visualization purposes). Rather, relative magnitude based features (e.g., amplitude of the R-peak relative to amplitude of the foot), time based features (see, e.g., FIG. 2) (e.g., time of the peak, time of the foot, and time of the peak slope), and/or shaped based features (e.g., beat matching) are used for beat classification.

A signal quality evaluation module 110 is executed, which determines whether the signal amplitude is a non-number value. If the signal amplitude is a non-number value (e.g., due to noisy or missing data), the signal is classified as noisy. If signal amplitude is not noise (i.e., comprises a number value), then the relative magnitude of the PPG peak amplitude is analyzed to determine whether the peak amplitude of the beat is greater than then amplitude at the foot of the beat. If this is not the case then the beat is classified as noisy. If the peak amplitude is greater than the foot amplitude, then a determination is made regarding whether the peak amplitude of the beat is also greater than the amplitude at peak slope of the beat and whether the amplitude at the foot of the beat is smaller than the amplitude at peak slope of the beat. If these conditions are not satisfied then the beat is classified as noisy.

Next, the signal quality evaluation module 110 determines whether wave feature timing meets predefined criteria. In a typical PPG beat (see, e.g., FIG. 2), the foot of the signal occurs before the peak slope, which occurs before the peak occurs. If this timing sequence is not seen in a particular beat, then the beat is classified as noisy. If the timing of the wave feature meets the predefined criteria, then a determination is made regarding whether more than one peak is present in the beat. If more than one peak is detected in a single beat, then the beat is classified as noisy.

If only one peak is present in the beat, then outlier data in the time-based feature data is removed. For instance, a probability distribution (e.g., a histogram) is estimated for each of the features derived from the ECG and PPG signals (e.g., PTTp, PTTs, PTTf, etc.). In one embodiment, the 5th and 95th percentile for each of these distributions is calculated to define upper and lower thresholds. An outlier is identified if the value of a feature is below or above the corresponding threshold. Beats with outliers are classified as noisy.

For remaining beats, the signal quality evaluation module 110 determines whether heart rate values are within a predetermined heart rate range. In one embodiment, the heart rate range ranges from 20 beats per minute to 200 beats per minute. However, it will be understood that any suitable range may be employed in conjunction with the various systems and methods described herein. Since PPG signal classification and quantification depends on ECG derived heart rate identification, heart rates beyond physiologic limits (i.e., the predetermined heart rate range) are rejected. Any beat with heart rate values outside this range is classified as noisy.

If the heart rate value is within the predetermined heart rate range, then beat matching is performed. The classification of beats in the PPG signal thus comprises two (or more) iterations. The first iteration is used to search for clean beat candidates across the PPG waveform. The second iteration is used to refine the results as a final classification of beats. Thus, a "beat template" is calculated by first interpolating and low-pass filtering each beat candidate, and then by averaging all beat candidates together. This "beat template" is subsequently used for searching beats across the PPG waveform to identify beats that match the "beat template". Beats that pass the matching threshold are classified as "clean" beats. The processor 100 combines the waveform evaluation results to classify each beat as clean or noisy and outputs the results, at 112. The processor then calculates and outputs overall signal statistics (e.g., number of clean waveforms, number of noisy waveforms, locations thereof within the PPG signal, etc.), at 114. Information output by the processor can be displayed to a user on a display 116 (e.g., a computer, workstation, handheld device, or the like).

It will be understood that the processor 100 executes, and the memory 102 stores, computer executable instructions for carrying out the various functions and/or methods described herein. The memory 102 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 100 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hard-wired electronic or logic circuit such as a discrete element circuit, a programmable logic device such as a PLD, PLA, FPGA, Graphics processing unit (GPU), or PAL, or the like.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates automatically detecting segments of clean photoplethysmography (PPG) signal and rejecting noisy PPG signal segments, comprising:
 a patient monitor that concurrently records unfiltered PPG signal and electrocardiograph signal (ECG) of a patient;
 a beat identification module configured to:
  receive as input the unfiltered PPG signal and concurrent ECG signal from the patient monitor;
  segment each of a plurality of heartbeats in the PPG signal using the concurrently measured ECG signal;

a PPG feature extraction module configured to extract a set of features for each heartbeat in the PPG signal, the features comprising one or more waveform amplitudes and one or more pulse transitions times (PPT);

a signal quality evaluation module configured to evaluate the extracted features and classify each PPG heartbeat waveform as clean or noisy, wherein the signal quality evaluation module does not utilize a motion signal for said evaluation; and a processor configured to output, on a display PPG signal statistics comprising identified clean PPG heartbeat waveforms for presentation to a user;

wherein the PPG feature extraction module is further configured to extract PPG signal features for each PPG heartbeat waveform comprising peak amplitude and peak slope amplitude; and wherein the signal quality evaluation module is further configured to, for each PPG heartbeat waveform, classify the PPG heartbeat waveform as noisy upon a determination that the peak amplitude of the heartbeat waveform is not greater than the amplitude at peak slope of the heartbeat waveform.

2. The system according to claim 1, wherein the beat identification module is further configured to identify an R-peak in each ECG heartbeat waveform, and identify between each pair of contiguous R-peaks a corresponding PPG heartbeat waveform in the concurrently captured PPG signal.

3. The system according to claim 1, wherein the PPG feature extraction module is further configured to extract PPG signal features for each PPG heartbeat waveform comprising:
- peak foot amplitude;
- peak pulse transit time (PTTp);
- foot pulse transit time (PTTf); and
- slope pulse transit time (PTTs).

4. The system according to claim 3, wherein the signal quality evaluation module is further configured to, for each PPG heartbeat waveform:
classify the PPG heartbeat waveform as noisy if the peak amplitude of the heartbeat waveform is a non-number value.

5. The system according to claim 4, wherein the signal quality evaluation module is further configured to, for each PPG heartbeat waveform:
classify the PPG heartbeat waveform as noisy if the peak amplitude of the heartbeat waveform is not greater than the amplitude at the foot of the heartbeat waveform.

6. The system according to claim 5, wherein the signal quality evaluation module is further configured to, for each PPG heartbeat waveform:
classify the PPG heartbeat waveform as noisy if the amplitude at the foot of the heartbeat waveform is not smaller than the amplitude at peak slope of the heartbeat waveform.

7. The system according to claim 6, wherein the signal quality evaluation module is further configured to, for each PPG heartbeat waveform:
classify the PPG heartbeat waveform as noisy if the foot of the heartbeat waveform occurs before the peak slope of the heartbeat waveform, or if the peak slope of the heartbeat waveform occurs before the waveform peak occurs.

8. The system according to claim 7, wherein the signal quality evaluation module is further configured to, for each PPG heartbeat waveform:

classify the PPG heartbeat waveform as noisy if more than one peak is detected in a single heartbeat waveform.

9. The system according to claim 8, wherein the signal quality evaluation module is further configured to, for each PPG heartbeat waveform:
- calculate a probability distribution for each extracted feature of the PPG waveform;
- define an upper threshold and a lower threshold for the probability distribution, and
- classify the PPG heartbeat waveform as noisy if one or more of the extracted features comprises a value outside of the upper or lower thresholds.

10. The system according to claim 9, wherein the lower threshold is 5% and the upper threshold is 95%.

11. The system according to claim 9, wherein the signal quality evaluation module is further configured to, for each PPG heartbeat waveform:
classify the PPG heartbeat waveform as noisy if the heart rate indicated by at least one of the ECG signal and the PPG signal is outside of a predetermined heart rate range.

12. The system according to claim 11, wherein the signal quality evaluation module is further configured to, for each PPG heartbeat waveform:
- execute a beat matching protocol whereby heartbeat waveforms not classified as noisy are compared to a predetermined heartbeat template; and
- classify the PPG heartbeat waveform as clean if PPG heartbeat waveform matches the heartbeat template.

13. A method for automatically detecting segments of clean photoplethysmography (PPG) signal and rejecting noisy PPG signal segments, comprising:
- receiving as input unfiltered PPG signal and concurrent ECG signal from a patient monitor;
- segmenting each of a plurality of heartbeats in the PPG signal using the concurrently measured ECG signal;
- extracting a set of features for each heartbeat in the PPG signal, the features comprising one or more waveform amplitudes and one or more pulse transitions times (PPT);
- evaluating the extracted features and classifying each PPG heartbeat waveform as clean or noisy, wherein evaluating and classifying do not utilize a motion signal; and
- outputting, on a display, PPG signal statistics comprising identified clean PPG heartbeat waveforms for presentation to a user;
- wherein the extracted PPG signal features for each PPG heartbeat waveform comprise peak amplitude, and peak slope amplitude;
- and further comprising classifying the PPG heartbeat waveform as noisy upon a determination that the peak amplitude of the heartbeat waveform is not greater than the amplitude at peak slope of the heartbeat waveform.

14. The method according to claim 13, further comprising identifying an R-peak in each ECG heartbeat waveform, and identifying between each pair of contiguous R-peaks a corresponding PPG heartbeat waveform in the concurrently captured PPG signal.

15. The method according to claim 13, wherein the extracted PPG signal features for each PPG heartbeat waveform further comprise:
- peak foot amplitude;
- peak pulse transit time (PTTp);
- foot pulse transit time (PTTf); and
- slope pulse transit time (PTTs);

and further comprising one or more of:
- classifying the PPG heartbeat waveform as noisy if the peak amplitude of the heartbeat waveform is a non-number value;
- classifying the PPG heartbeat waveform as noisy if the peak amplitude of the heartbeat waveform is not greater than the amplitude at the foot of the heartbeat waveform;
- classifying the PPG heartbeat waveform as noisy if the peak amplitude of the heartbeat waveform is not greater than the amplitude at peak slope of the heartbeat waveform or if the amplitude at the foot of the heartbeat waveform is not smaller than the amplitude at peak slope of the heartbeat waveform;
- classifying the PPG heartbeat waveform as noisy if the foot of the heartbeat waveform occurs before the peak slope of the heartbeat waveform, or if the peak slope of the heartbeat waveform occurs before the waveform peak occurs;
- classifying the PPG heartbeat waveform as noisy if more than one peak is detected in a single heartbeat waveform;
- calculating a probability distribution for each extracted feature of the PPG waveform, defining an upper threshold and a lower threshold for the probability distribution, and classifying the PPG heartbeat waveform as noisy if one or more of the extracted features comprises a value outside of the upper or lower thresholds;
- classifying the PPG heartbeat waveform as noisy if the heart rate indicated by at least one of the ECG signal and the PPG signal is outside of a predetermined heart rate range; and
- executing a beat matching protocol whereby heartbeat waveforms not classified as noisy are compared to a predetermined heartbeat template, and classifying the PPG heartbeat waveform as clean if the PPG heartbeat waveform matches the heartbeat template.

16. A method for automatically detecting segments of clean photoplethysmography (PPG) signal and rejecting noisy PPG signal segments, comprising:
- receiving as input unfiltered PPG signal and concurrent electrocardiograph (ECG) signal from a patient monitor;
- segmenting each of a plurality of heartbeats in the PPG signal using the concurrently measured ECG signal;
- extracting a set of features for each heartbeat in the PPG signal, the features comprising one or more waveform amplitudes and one or more pulse transitions times (PPT);
- evaluating the extracted features and classifying each PPG heartbeat waveform as clean or noisy, wherein evaluating and classifying comprises: (i) a first iteration of classification to identify an initial plurality of clean PPG heartbeat waveforms; (ii) generating, using the identified initial plurality of clean PPG heartbeat waveforms, a heartbeat template; (iii) a second iteration of classification to classify some or all of the initial plurality of clean PPG heartbeat waveforms as finally clean by comparing each of the initial plurality of clean PPG heartbeat waveforms to the generated heartbeat template and classifying the PPG heartbeat waveform as claim if PPG heartbeat waveform matches the heartbeat template at or above a threshold; and
- outputting, on a display, PPG signal statistics comprising identified clean PPG heartbeat waveforms for presentation to a user;
- wherein the extracted PPG signal features for each PPG heartbeat waveform comprise peak amplitude, and peak slope amplitude.

* * * * *